United States Patent
Whitesides et al.

(10) Patent No.: US 9,594,051 B2
(45) Date of Patent: Mar. 14, 2017

(54) MICROFLUIDIC DEVICES FOR MULTIPLEXED ELECTROCHEMICAL DETECTION

(71) Applicant: President and Fellows of Harvard College, Cambridge, MA (US)

(72) Inventors: George M. Whitesides, Cambridge, MA (US); Xiujun Li, Cambridge, MA (US); Frederique Deiss, Cambridge, MA (US); Zhihong Nie, Cambridge, MA (US); Xinyu Liu, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 419 days.

(21) Appl. No.: 14/199,229

(22) Filed: Mar. 6, 2014

(65) Prior Publication Data

US 2014/0183059 A1    Jul. 3, 2014

Related U.S. Application Data

(63) Continuation of application No. PCT/US2012/053930, filed on Sep. 6, 2012.
(Continued)

(51) Int. Cl.
| | | |
|---|---|---|
| *G01N 27/416* | (2006.01) | |
| *B01L 3/00* | (2006.01) | |
| *G01N 27/327* | (2006.01) | |

(52) U.S. Cl.
CPC ...... *G01N 27/416* (2013.01); *B01L 3/502707* (2013.01); *B01L 3/502738* (2013.01);
(Continued)

(58) Field of Classification Search
None
See application file for complete search history.

(56) References Cited

U.S. PATENT DOCUMENTS 9,192,933 B2 * 11/2015 Whitesides ............. B01L 3/502

FOREIGN PATENT DOCUMENTS

| WO | WO-2007/096730 A1 | 8/2007 |
| WO | WO-2010/102279 A1 | 9/2010 |
| WO | WO-2010/124001 A1 | 10/2010 |

OTHER PUBLICATIONS

Dungchai, et al., Electrochemical Detection for Paper-Based Microfluidics, Analytical Chemistry, vol. 81, No. 14, Jul. 15, 2009, p. 5821-5826.*

(Continued)

*Primary Examiner* — J. Christopher Ball
(74) *Attorney, Agent, or Firm* — Wilmer Cutler Pickering Hale and Dorr LLP

(57) ABSTRACT

The multiplexed electrochemical microfluidic paper-based analytical device comprises multiple detection zones for the detection of multiple biochemical analytes from one single sample. Cavity valves integrated on the device will deliver the sample to different detection zones. These analytes include, but are not limited to, urea, creatinine, creatine, glucose, lactate, ethanol, uric acid, cholesterol, pyruvate, creatinine, β-hydroxybutyrate, alanine aminotrasferase, aspartate aminotransferase, alkaline phosphatase, and acetylcholinesterase (or its inhibitors). This system will provide a simple and low-cost POC approach to obtain quantitative and multiple biological information from one sample (e.g. one drop of blood).

55 Claims, 12 Drawing Sheets

Related U.S. Application Data

(60) Provisional application No. 61/531,423, filed on Sep. 6, 2011.

(52) U.S. Cl.
CPC .. *G01N 27/3272* (2013.01); *B01L 2300/0645* (2013.01); *B01L 2300/0825* (2013.01)

(56) References Cited

OTHER PUBLICATIONS

Li et al., Paper-Based Microfluidic Devices by Plasma Treatment, Analytical Chemistry, vol. 80, No. 23, Dec. 1, 2008, p. 9131-9134 + Supplementary Material.*

Carvalhal et al., Electrochemical Detection in a Paper-Based Separation Device, Analytical Chemistry, vol. 82, No. 3, Feb. 1, 2010, p. 1162-1165.*

Martinez, et al., Programmable diagnostic devices made from paper and tape, Lab on a Chip, vol. 10, Oct. 7, 2010, p. 2499-2504.*

Nie, et al., Electrochemical sensing in paper-based microfluidic devices, Lab on a Chip, vol. 10, Feb. 21, 2010, p. 477-483.*

International Search Report and Written Opinion issued by the European Patent Office as International Searching Authority for International Application No. PCT/US2012/053930 dated Jan. 31, 2013 (9 pages).

Nie, Z. et al., "Integration of paper-based microfluidic devices with commercial electrochemical readers," Lab Chip, vol. 10, pp. 3163-3169 (2010).

* cited by examiner

MICROFLUIDIC DEVICES FOR MULTIPLEXED ELECTROCHEMICAL DETECTION

RELATED APPLICATIONS

This application is a continuation application of and claims the benefit of priority to PCT International Application No. PCT/US12/53930, filed on Sep. 6, 2012, which claims priority to U.S. Provisional Patent Application No. 61/531,423, filed on Sep. 6, 2011, both of which are hereby incorporated by reference in their entirety.

INCORPORATION BY REFERENCE

All non-patent literature, patents, patent applications and publications cited herein are hereby incorporated by reference in their entirety in order to more fully describe the state of the art as known to those skilled therein as of the date of the invention described herein.

BACKGROUND

Point-of-care (POC) devices can bring the diagnostic test conveniently and immediately to patients, thus allowing for immediate clinical decisions to be made. The advent of POC testing since the 1980s has led to a revolution in clinical medicine and patient care. Those POC devices include glucose meters (glucometer), cholesterol meters, pregnancy test strips, and so on. Among those POC devices, the glucometer plays a significant role in patient home care, because of its ease to use, portability, fairly low cost, and the need from a large population of people with diabetes. The large population of people with diabetes has created a need leading to the optimization of home-testing glucose meter. The electrochemical glucose meter allows quantitative and sensitive quantification.

Those individual POC devices, however, can only measure one biomarker or analyte at a time. Thus, there remains a need for device capable of obtaining richer biomarker or analyte information out of one sample.

SUMMARY

Described herein is a microfluidic, electrochemical device for conducting multiple electrochemical assays on a single device. Only one sample is required to perform multiple analysis. Also described herein is a microfluidic device for use in electrochemical assays other than glucose detection.

In one aspect, the microfluidic, electrochemical device includes a first porous, hydrophilic layer comprising a fluid-impermeable material that defines at least a first test channel and a deposition zone within the first porous, hydrophilic layer. The device also comprises a second porous, hydrophilic layer disposed over the first layer comprising a fluid-impermeable material that defines at least a first reaction zone including one or more reagents for reacting with a first analyte, the deposition zone in fluid communication with the first reaction zone through the first test channel; and a first electrode assembly comprising one or more electrode(s) in fluidic communication with the first reaction zone, said electrodes sized to provide current signals readable by a glucose meter (also called "Glucometer") or other commercial electrochemical readers; wherein the first analyte is not glucose, and wherein at least a portion of the device is sized and arranged to be insertable into a glucose meter. Additionally, the device may be a multiplexed device further comprising one or more additional test channel(s) on the first porous hydrophilic layer in fluidic communication with the deposition zone, additional reaction zone(s) on the second layer, and additional electrode assemblies in fluidic communication with the additional reaction zones. Each reaction zone is capable of fluidic communication with a corresponding test channel through a valve system. The valve is capable moving from a first non-fluid-communicating position to a second fluid-communicating position. In the first non-fluid-communication position, the reaction zone and the test channel are not in fluidic communication. In the second fluid-communication position, the reaction zone and the test channel are in fluidic communication. Accordingly, a sample deposited in the deposition zone may flow into a specific reaction zone in a controlled manner, e.g., by activating the valve between the reaction zone and the test channel. Thus, a single sample containing a plurality of analytes can be directed to different reaction zones containing different testing agents, so that different analytes of the same sample will be analyzed in different reaction zones.

In one aspect, a microfluidic, electrochemical device is described, comprising one or more porous, hydrophilic layer comprising a fluid-impermeable material that defines at least a first test channel and a deposition zone within the porous, hydrophilic layer;

at least a first reaction zone for detecting a first analyte and defined by a fluid impermeable material in a porous hydrophobic layer, the first reaction zone in fluid communication with the deposition zone through the first test channel; and a first electrode assembly comprising one or more electrode(s) in fluidic communication with the first reaction zone, said electrodes sized to provide current signals readable or detectable by an electrochemical reader;

wherein the deposition zone, the first reaction zone and the first electrode assembly are on the same or different hydrophilic layers, wherein the first analyte is not glucose, and wherein at least a portion of the device is sized and arranged to be insertable into an electrochemical reader.

In any of the preceding embodiments, the first reaction zone includes one or more reagents for detecting the first analyte.

In any of the preceding embodiments, the first analyte is selected from the group consisting of lactate, ethanol, uric acid, urea, creatinine, creatine, glucose, cholesterol, pyruvate, creatinine, β-hydroxybutyrate, alanine aminotransferase, aspartate aminotransferase, alkaline phosphatase, and acetylcholinesterase (or its inhibitors).

In any of the preceding embodiments, the microfluidic, electrochemical device further comprises a second test channel defined by the fluid impermeable material; and a second reaction zone for detecting a second analyte and defined by a fluid impermeable material in a porous hydrophobic layer, the second reaction zone in fluid communication with the deposition zone through the second test channel; and a second electrode assembly comprising one or more electrode(s) in fluidic communication with the second reaction zone, said electrodes sized to provide current signals readable by an electrochemical reader.

In any of the preceding embodiments, the second reaction zone includes one or more reagents for detecting the second analyte.

In any of the preceding embodiments, the first and the second analytes are the same or different.

In any of the preceding embodiments, the second analyte is not glucose.

In any of the preceding embodiments, the second analyte is selected from the group consisting of lactate, ethanol, uric acid, urea, creatinine, creatine, glucose, cholesterol, pyruvate, creatinine, β-hydroxybutyrate, alanine aminotransferase, aspartate aminotransferase, alkaline phosphatase, and acetylcholinesterase (or its inhibitors).

In any of the preceding embodiments, the microfluidic, electrochemical device further comprises a third test channel defined by the fluid impermeable material; and a third reaction zone for detecting a third analyte and defined by a fluid impermeable material in a porous hydrophobic layer, the third reaction zone in fluid communication with the deposition zone through the third test channel; and a third electrode assembly comprising one or more electrode(s) in fluidic communication with the third reaction zone, said electrodes sized to provide current signals readable by an electrochemical reader.

In any of the preceding embodiments, the third reaction zone includes one or more reagents for detecting the third analyte.

In any of the preceding embodiments, the first, second, and third analytes are the same or different.

In any of the preceding embodiments, the third analyte is not glucose.

In any of the preceding embodiments, the third analyte is selected from the group consisting of lactate, ethanol, uric acid, urea, creatinine, creatine, glucose, cholesterol, pyruvate, creatinine, β-hydroxybutyrate, alanine aminotransferase, aspartate aminotransferase, alkaline phosphatase, and acetylcholinesterase (or its inhibitors).

In any of the preceding embodiments, the microfluidic, electrochemical device further comprises additional test channel(s) defined by the fluid impermeable material; and additional reaction zone(s) for detecting additional analyte(s) and defined by a fluid impermeable material in a porous hydrophobic layer, the reaction zone in fluid communication with the deposition zone through the test channel; and additional electrode assemblies each comprising one or more electrode(s) in fluidic communication with the respective reaction zone, said electrodes sized to provide current signals readable by an electrochemical reader.

In any of the preceding embodiments, the additional reaction zone includes one or more reagents for detecting the additional analytes.

In any of the preceding embodiments, wherein the first, second, third, and additional analytes are the same or different.

In any of the preceding embodiments, the additional analyte(s) are not glucose.

In any of the preceding embodiments, additional analyte is selected from the group consisting of lactate, ethanol, uric acid, urea, creatinine, creatine, glucose, cholesterol, pyruvate, creatinine, β-hydroxybutyrate, alanine aminotransferase, aspartate aminotransferase, alkaline phosphatase, and acetylcholinesterase (or its inhibitors).

In any of the preceding embodiments, the microfluidic, electrochemical device comprises at least 12 test channels; and at least 12 reaction zones for detecting 12 analyte(s), respectively, and each of the reaction zone is in fluid communication with the deposition zone through the respective test channels; and at least 12 electrode assemblies each comprising one or more electrode(s) in fluidic communication with the respective reaction zone, said electrodes sized to provide current signals readable by an electrochemical reader.

In any of the preceding embodiments, the deposition zone and each of the reaction zone(s) are in fluid contact through a valve capable moving from a first non-fluid-communicating position to a second fluid-communicating position.

In any of the preceding embodiments, the deposition zone and any of the reaction zone are not in fluid communication when the valve connecting the deposition zone and the reaction zone is at the first non-fluid-communicating position.

In any of the preceding embodiments, the valve comprises a spacer layer disposed between the first and second porous, hydrophilic layers, said spacer layer comprising an opening in alignment with at least a portion of the respective reaction zone and testing channel.

In any of the preceding embodiments, the reagent is selected to react with the analyte to generate an intermediate reducible or oxidizable by the electrode.

In any of the preceding embodiments, the analyte is reduced or oxidized.

In any of the preceding embodiments, the hydrophilic layer comprises paper.

In any of the preceding embodiments, the fluid-impermeable material comprises polymerized photoresist.

In any of the preceding embodiments, wherein the electrochemical reader is a glucose meter.

In another aspect, a method of detecting a first analyte is described, comprising:

providing the device as described herein capable of detecting a first analyte;

depositing a fluidic sample in the depositing zone;

contacting the device with an electrochemical reader; and obtaining a readout by the electrochemical reader indicative of the concentration of the first analyte based on a first set of instructions.

In yet another aspect, a method of detecting a first and a second analytes, comprising:

providing the device as described herein capable of detecting first and second analytes;

depositing a fluidic sample in the depositing zone;

contacting the device with an electrochemical reader;

obtaining a readout by the electrochemical reader indicative of the concentration of the first analyte based on a first set of instructions; and obtaining a readout by the electrochemical reader indicative of the concentration of the second analyte based on a second set of instructions.

In yet another aspect, a method of detecting a first, second, and additional analyte(s), comprising:

providing the device as described herein capable of detecting first, second and third analytes;

depositing a fluidic sample in the depositing zone;

contacting the device with an electrochemical reader;

obtaining a readout by the electrochemical reader indicative of the concentration of the first analyte based on a first set of instructions;

obtaining a readout by the electrochemical reader indicative of the concentration of the second analyte based on a second set of instructions; and obtaining readout(s) by the electrochemical reader indicative of the concentration of the third analyte based on a additional set(s) of instructions.

In any of the preceding embodiments, the method further comprises:

actuating a valve from a first non-fluid communicating position to a second fluid-communicating position to enable fluid contact between the deposition zone and the reaction zone(s).

In yet another aspect, a kit is described, comprising:
a microfluidic, electrochemical device comprising
a first porous, hydrophilic layer comprising a fluid-impermeable material that defines at least a first test channel and a deposition zone within the first porous, hydrophilic layer;
a second porous, hydrophilic layer disposed over the first layer comprising:
  a fluid-impermeable material that defines at least a first reaction zone including one or more reagents for detecting a first analyte, the deposition zone in fluid communication with the first reaction zone through the first test channel; and
  a first electrode assembly comprising one or more electrode(s) in fluidic communication with the first reaction zone, said electrodes sized to provide current signals readable by an electrochemical reader; and
a first set of instructions for obtaining a readout by the electrochemical reader for a characteristic of the first analyte, wherein the first analyte is not glucose.

In any of the preceding embodiments, the first set of instructions indicates a relation between a current readout by the electrochemical reader and a concentration of the first analyte.

In any of the preceding embodiments, the first analyte is selected from the group consisting of lactate, ethanol, uric acid, urea, creatinine, creatine, glucose, cholesterol, pyruvate, creatinine, β-hydroxybutyrate, alanine aminotrasferase, aspartate aminotransferase, alkaline phosphatase, and acetylcholinesterase (or its inhibitors).

In any of the preceding embodiments, the first porous, hydrophilic layer further comprises a second test channel; and
  the second porous, hydrophilic layer further comprises
  a second reaction zone including one or more reagents for detecting a second analyte, the deposition zone in fluid communication with the second reaction zone through the second test channel; and
  a second electrode assembly comprising one or more electrode(s) in fluidic communication with the second reaction zone, said electrodes sized to provide current signals readable by an electrochemical reader; and
  the kit further comprises a second set of instructions for obtaining a readout by the electrochemical reader for a characteristic of the second analyte.

In any of the preceding embodiments, the second set of instructions indicates a relation between a current readout by the electrochemical reader and a concentration of the second analyte.

In any of the preceding embodiments, the first and the second analytes are the same or different.

In any of the preceding embodiments, the second analyte is not glucose.

In any of the preceding embodiments, the first or second analyte is selected from the group consisting of lactate, ethanol, uric acid, urea, creatinine, creatine, glucose, cholesterol, pyruvate, creatinine, β-hydroxybutyrate, alanine aminotrasferase, aspartate aminotransferase, alkaline phosphatase, and acetylcholinesterase (or its inhibitors).

In any of the preceding embodiments,
the first porous, hydrophilic layer further comprises a third test channel; and
the second porous, hydrophilic layer further comprises:
  a third reaction zone each including one or more reagents for detecting a third analyte, the deposition zone in fluid communication with the third reaction zone through the third test channel; and
  a third electrode assembly comprising one or more electrode(s) in fluidic communication with the third reaction zone, said electrodes sized to provide current signals readable by an electrochemical reader; and
the kit further comprises a third set of instructions for obtaining readouts by electrochemical reader for a characteristic of the third analyte.

In any of the preceding embodiments, the third set of instructions indicates a relation between a current readout by the electrochemical reader and a concentration of each additional analyte.

In any of the preceding embodiments, the first, second, and third analytes are the same or different.

In any of the preceding embodiments, the third analyte is not glucose.

In any of the preceding embodiments, the first, second, or third analyte is selected from the group consisting of lactate, ethanol, uric acid, urea, creatinine, creatine, glucose, cholesterol, pyruvate, creatinine, β-hydroxybutyrate, alanine aminotrasferase, aspartate aminotransferase, alkaline phosphatase, and acetylcholinesterase (or its inhibitors).

In any of the preceding embodiments, the first porous, hydrophilic layer further comprises additional test channel(s); and
  the second porous, hydrophilic layer further comprises:
  additional reaction zone(s) each including one or more reagents for detecting additional analyte(s), the deposition zone in fluid communication with the additional reaction zone(s) through the respective additional test channel(s); and
  additional electrode assemblies each comprising one or more electrode(s) in fluidic communication with the respective additional reaction zone, said electrodes sized to provide current signals readable by an electrochemical reader; and
  the kit further comprises additional set(s) of instructions for obtaining readout(s) by the electrochemical reader for a characteristic of the additional analyte(s).

In any of the preceding embodiments, the additional set(s) of instructions indicate a relation between a current readout by the electrochemical reader and a concentration of each additional analyte.

In any of the preceding embodiments, the first, second, third, and additional analytes are the same or different.

In any of the preceding embodiments, the additional analyte(s) are not glucose.

In any of the preceding embodiments, the first, second, third, or additional analyte is selected from the group consisting of lactate, ethanol, urea, creatinine, creatine, glucose, cholesterol, pyruvate, creatinine, β-hydroxybutyrate, alanine aminotrasferase, aspartate aminotransferase, alkaline phosphatase, and acetylcholinesterase (or its inhibitors).

In any of the preceding embodiments, the first porous, hydrophilic layer comprises at least 12 test channels;
the second porous, hydrophilic layer comprises
at least 12 reaction zone(s) each including one or more reagents for detecting 12 analytes, the deposition zone in fluid communication with the reaction zones through the respective test channels; and
at least 12 electrode assemblies each comprising one or more electrode(s) in fluidic communication with the respective reaction zone, said electrodes sized to provide current signals readable by an electrochemical reader; and
the kit further comprises at least 12 set(s) of instructions for obtaining readout(s) by the electrochemical reader for a characteristic of the 12 analyte(s), respectively.

In any of the preceding embodiments, the deposition zone and each of the reaction zone(s) are in fluid contact through a valve capable moving from a first non-fluid-communicating position to a second fluid-communicating position. The deposition zone and any of the reaction zone are not in fluid communication when the valve connecting the deposition zone and the reaction zone is at the first non-fluid-communicating position. In any of the preceding embodiments, the valve comprises a spacer layer disposed between the first and second porous, hydrophilic layers, said spacer layer comprising an opening in alignment with at least a portion of the respective reaction zone and testing channel.

In any of the preceding embodiments, the reagent is selected to react with the analyte to generate an intermediate reducible or oxidizable by the electrode.

In any of the preceding embodiments, the hydrophilic layer comprises paper.

In any of the preceding embodiments, the fluid-impermeable material comprises polymerized photoresist. In any of the preceding embodiments, the electrochemical reader is a glucose meter.

As used herein, an electrochemical reader refers to a device capable of performing an electrochemical analysis, including but are not limited to inducing electrochemical reactions at the electrodes and measuring the current and/or potential resulting of those reactions, and to display the result.

BRIEF DESCRIPTION OF THE DRAWING

The subject matter is described with reference to the following figures, which are presented for the purpose of illustration only and are not intended to be limiting of the invention.

FIG. 3(a) the principle of cavity valves; FIG. 3(b) a turned-on valve which enables fluidic communication.

FIG. 4 illustrates photos showing the delivery of a red food dye sample to different reaction zones of a microfluidic device with three testing strips using the "push-button" cavity valves to control fluids for multiplexed assay using a glucometer. (a) before sample loading; (b) sample loaded; (c) the central valve was actuated to be on; and (d) the left valve was actuated to be on.

DETAILED DESCRIPTION

Described herein is microfluidic device that at least one electrode assembly, one testing channel, and one reaction zone. The electrode assembly, testing channel, and reaction zone are deposited on hydrophilic layers patterned by fluid-impermeable materials that define one or more hydrophilic channels or regions on the patterned hydrophilic layer. The method of preparing patterned hydrophilic layers is described in details in PCT Publication No. 2008/049083, the content of which is incorporated in its entirety by reference. The method of preparing microfluidic device including one or more electrode assemblies is described in details in PCT Application No. PCT/US2010/026499, the content of which is incorporated in its entirety by reference. The electrode assembly is deposited on a portion of the hydrophilic layer that is shaped so that it may fit into an electrochemical reader, such as a glucose meter. The test strip comprises at least an electrode assembly which is in fluidic communication with a reaction zone and optionally one or more hydrophilic channels or regions.

In some embodiments, the microfluidic device comprises two or more test strips, and each test strip is sized and shaped to be readable by a glucose meter. Each test strip comprises an electrode assembly and a reaction zone. In some embodiments, the reaction zone may have reagents predeposited so that when a sample containing one or more analytes flows into the reaction zone, the analytes react with the predeposited reagents, thereby generating a current measurable by a glucose meter or other electrochemical readers. In other embodiments, the analyte may react with the predeposited reagents to generate intermediate that ae used to generate a measurable current. The use of other commercial electronic readers is also contemplated. Also, electronic readers developed specifically for use with the microfluidic electrochemical device described herein is contemplated.

In other embodiments, the reaction zone may have no pre-deposited reagents and the reactions between the analyte and reagent occurs in other hydrophilic regions in fluidic communication with the reaction zone, or the analyte itself is detected by the electrode assembly.

When the microfluidic device includes two or more testing strips, a user can obtain high-density biological information from a single sample. Each testing strip can be designed to test different analyte and may contain a reaction zone with pre-deposited reagents for the testing of that analyte. Thus, a user using the microfluidic device as described herein can test a range of different analytes from a single biological sample, such as blood, urine, or other body fluids. The microfluidic device may contain 2, 3, 4, 5, 6, 7, 8, 9, 10, 11, 12, or more test strips.

Figure 1:
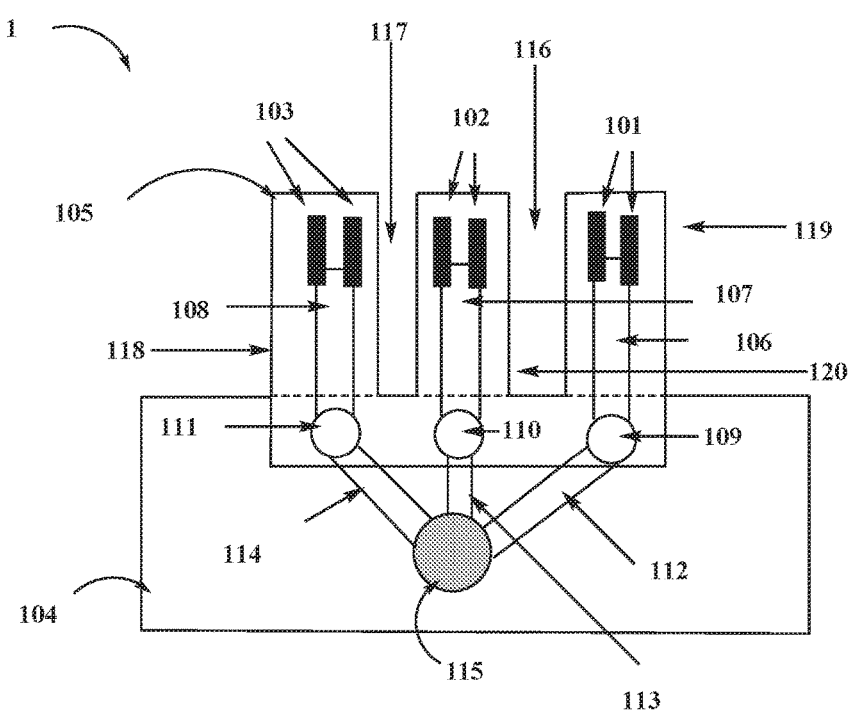
FIG. 1 illustrates a multiplexed microfluidic, electrochemical device containing three sets of reaction zones, test channels, and electrode assemblies.

A microfluidic device having multiple test strips according to some embodiments is described with reference to FIG. 1. As shown in FIG. 1, the microfluidic device 1 has a first porous hydrophilic layer 104 at least partially overlaid with a second porous hydrophilic layer 105. Layer 104 is patterned by a fluid-impermeable material to define a hydrophilic deposition zone 115 and a first, second, and third test channels 112, 113, and 114, respectively. In use, a fluidic sample is deposited in the deposition zone 115, which is in fluidic communication with the channels 112, 113, and 114. The second porous hydrophilic layer 105 contains defined first, second, and third reaction zones 106, 107, and 108. Each of the first, second, and third reaction zones 106, 107, and 108 can be brought into fluidic communication with first, second, and third test channels 112, 113, and 114, respectively. The layer 105 also contains an electrode assembly 101 in fluidic communication with the first reaction zone 106, an electrode assembly 102 in fluidic communication with the second reaction zone 107, and an electrode assembly 103 in fluidic communication with the third reaction zone 108. Each of the reaction zones 106-108 may have different reagent pre-deposited in the zones designed to react with a particular type of analyte and generate an electrical signal that is readable by an electrochemical reader, e.g., a glucose meter. Thus, the device as shown in FIG. 1 can be used to test three different analytes from a single biological sample. Microfluidic devices containing 4 or more testing strips in one device are contemplated. Also, for purpose of simplicity, two electrodes are shown for each electrode assembly in device 1. Electrode assemblies with 3 or more electrodes, e.g., positive, negative and reference electrodes, are contemplated. In some embodiments, the electrode assembly includes four electrodes. As used herein, the phrase "detection zone" and "reaction zone" are used interchangeably.

The device as shown in FIG. 1 provides valves for controlling fluid flow in the microfluidic electrochemical device. In some embodiments, first reaction zone 106 is partially overlapped with the first test channel 112 and the overlapped portion contains valve 109. Valve 109 is capable of moving from a first non-fluid-communicating (open) position to a second fluid-communicating (closed) position. Optionally, a fluid impermeable spacer layer (layer 121 in FIG. 3A) may be placed between layers 104 and 105. When valve 109 is in the open position, test channel 112 and reaction zone 106 are not in fluidic contact and so that sample is prevented from reaching reaction zone 106. When valve 109 is in the closed position, test channel 112 and reaction zone 106 are in fluidic contact and so that sample deposited in deposition zone 115 can flow into reaction zone 106, for example, by capillary action. Similarly, valve 110 is located at the overlapped portion of the second test channel 113 and the second reaction zone 107 and valve 111 is located at the overlapped portion of the second test channel 114 and the second reaction zone 108. Valves 110 and 111 functions similarly to valve 109 and control the fluidic communication between the respective test channel and reaction zone. Thus, a user, at his or her discretion, may selectively active any of the valves 109-111 and thus enable the respective test channel and reaction zone. In the reaction zone connected to an activated valve, i.e., the reaction zone having fluidic contact with its respective testing channel, a particular analyte reacts with reagents pre-deposited in that reaction zone and generates a signal readable by the glucose meter.

The three "testing strips" 118, 119, and 120 as shown in FIG. 1 are part of the same patterned layer 105. The layer 105 has opening 117 and 116 so that each testing strip can be inserted into a glucose meter separately. In some embodiments, a valve mechanism is used to selectively "activate" each testing strip in a controlled manner so that each testing strip can be read when it is inserted into the glucose meter or any other electrochemical reader.

Figure 3:
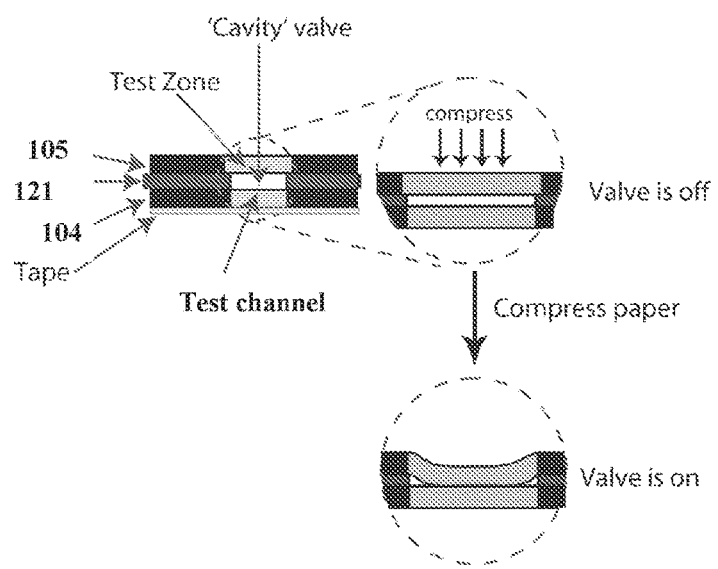
FIG. 3 is schematics of a cross-section view of cavity valves.
Figure 3:
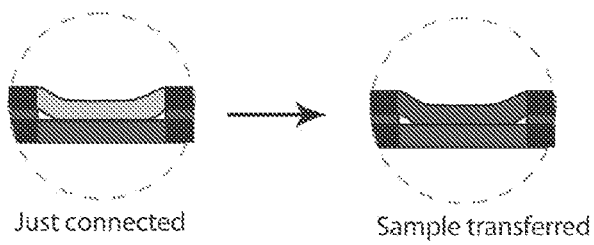

A detailed mechanism of the valve mechanism is illustrated with reference to FIG. 3. FIG. 3A shows layer 105, e.g., a paper layer, comprising a test zone is overlaid with bottom layer 104 comprising a test channel. There may be a spacer layer 121, e.g., a plastic or tape layer, in between the two paper layers having an opening, i.e., "cavity" valve. When the valve is not pressed, i.e., the valve is off, there is no fluidic communication between the test zone and the test channel (also referred to as non-fluid-communication position above). Conversely, when the valve is pressed, i.e., the valve is on, there is fluidic communication between the test zone and the test channel (also referred to as fluid-communication position above) (FIG. 3A). Once the valve is activated, the fluid sample in the bottom layer is transferred to the top layer as is illustrated in FIG. 3B.

Thus, the cavity valves (alternatively described herein as "Push-buttons") are used to deliver the sample to different test zones individually for multiplexed assays. Because the glucose meter may only allow one readout at a time, the device described herein enables the delivery of sample to the individual test zone one by one. A user can press the cavity valve for a particular testing strip to actuate the 'button' to be on, thus delivering the sample for the be tested by that testing strip, while the sample for the assays of other analytes located in different channels are still waiting in the queue for the subsequent assays. This design allows multiplexed electrochemical detection on microfluidic devices using a glucose meter in a controlled fashion.

Some portable electrochemical reader, such as the current commercial CVS glucometer True Track™, are fully automated for an easy use. Once the test strip is inserted in the port of the glucometer, the glucometer will be able to detect when the sample is in the detection zone to launch the 10 sec countdown. A combination of auxiliaries electrodes in addition to the two electrodes used afterwards for the electrochemical measurement (in some embodiments an assembly of four electrodes, but not limited to such number) allows the detection of the fluid in different areas of the detection zone. In addition to time the reaction and detection after wicking of the sample into the detection zone, this system prevents the user to re-use a test strip or invalids a result (display errors) if a too small volume of sample is deposited (The whole volume of the detection zone is not being filled after a certain elapsed time of the countdown, so the fluid is not in contact with all the electrodes of the assembly). These features are important for a home-testing point of view and for use in a ressource limited settings as they allow people with minimum training to use such point-of-care device with confidence. The electrochemical microfluidic analytical devices presented here keep the same features, although for a device with more than one detection zone, a valve to prevent the fluid (sample) to wick into the detection zone before the test strip corresponding to this particular detection zone is inserted inside the port of the glucometer. Without the control of the fluid, especially when and where the fluid is going on the different detection zones, a test strip could be considered as already used by such electrochemical reader as the electrodes assembly will detect a fluid being present in the detection zone at the initialization step (when the test strip is inserted).

It is also contemplated to have the assembly of one or more electrode(s) to be disposed in various spatial configurations to allow the detection of a fluid at other area of the device or for other timing applications (such as starting the countdown when the fluid reach a specific part of the incubation channel or a specific area of the detection zone).

In some embodiments, the electrodes corresponding to the auxiliaries one out of the four represented are the two vertical ones. The main electrodes used at the end of the countdown for the quantification of the intermediate are the two horizontal ones, between which the potential to induce the electrochemical reaction is applied.

The device, kit, and method described herein can be used to analyze glucose or non-glucose analytes. Other non-glucose analytes include lactate, ethanol, urea, creatinine, creatine, uric acid, cholesterol, pyruvate, creatinine, β-hydroxybutyrate, alanine aminotrasferase, aspartate aminotransferase, alkaline phosphatase, and acetylcholinesterase (or its inhibitors). Suitable reagents pre-deposited on the hydrophilic regions of the microfludic device for these non-glucose analytes are chosen so that the reaction between the non-glucose analyte and the reagent will generate a current readable by the glucose meter or other commercial electrochemical readers, where a potential is applied by the electrochemical reader. In some embodiments, the reactions occur in the reaction zones are enzymatic-based reactions. The enzyme can be specific to the analyte to be quantified and an electrochemical mediator (such as $Fe(CN)_6^{3-}$) may undergo a concomitant reaction (to become $Fe(CN)_6^{4-}$) and then be electrochemically quantified by the glucosemeter. Any other electroactive species able to react at the potential applied by the glucometer is suitable. For instance, for the glucometer, a potential of 0.5V can be applied. In some embodiments, the glucose meter is CVSglucometer TrueTrack™ glucosemeter. Different potential range for other electrochemical reader can be used. Other examples of such chemical species include ruthenium hexamine and Os(III) complex. These chemical species can be recognized by a commercial electrochemical reader, e.g., a glucose meter, and thus one or more reagent can be selected to be predeposited in the hydrophilic regions to react with non-glucose analytes to generate these chemical species.

In some embodiments, the device, kit, and method described herein can be used to analyze the ratios and concentrations of multiple analytes within the same sample. In some embodiments, blood urea nitrogen/creatinine ratio can be measured.

In some embodiments, electrochemical reader, as used herein, refers to an amperometric device which detects the existence of certain analytes.

In some embodiments, the patterned hydrophilic layer is a patterned paper layer. The paper-based 3D microfluidic device for multiplexed assay has several significant features: (i) it is fairly inexpensive, in terms of cost for materials of devices (paper is the main substrate) and the electrochemical reader; it takes the advantage of the well-developed, commercially available, and inexpensive glucose meters, without spending a large amount of expenditure or sophisticated engineering work to develop new electrochemical readers; (ii) it provides higher density of biomarker information than other POC devices commercially available; a variety of biological markers such as lactate, ethanol, uric acid, urea, creatinine, creatine, glucose, cholesterol, pyruvate, creatinine, β-hydroxybutyrate, alanine aminotrasferase, aspartate aminotransferase, alkaline phosphatase, and acetylcholinesterase (or its inhibitors) can be tested from one sample; (iii) it is portable; (iv) cavity valves can be included in such a device to control fluids, without the use of any complicated pneumatic setup and external electric source; (v) it can provide multiple replicas of data from a single run assay, if each testing strip is designed to test the same analyte; (vi) the assays are programmable, which allows patients to perform an individual analysis or measure different combinations of analytes.

In some embodiments, paper is used as the substrate for electrochemical detection because it is inexpensive, and easy to pattern channels using wax printing. Electrodes can be screen-printed electrodes using conductive carbon ink, and wires using silver ink because of its good conductivity. Carbon ink can also be used for wire material as well. The electrodes made from conductive ink have several advantages: (i) they are less expensive, compared to Au or Pt electrodes; (ii) the fabrication process is simple, and has less requirements on cleanroom facilities; (iii) those materials are well developed, and easy to obtain, because they are widely used in both industrial and academic research; (iv) screen printing is capable of mass production at low cost.

Porous, hydrophilic layers include any hydrophilic substrate that wicks fluids by capillary action. In one or more embodiments, the porous, hydrophilic layer is paper. Non-limiting examples of porous, hydrophilic layers include chromatographic paper, filter paper, nitrocellulose and cellulose acetate, cellulosic paper, filter paper, paper towels, toilet paper, tissue paper, notebook paper, Kim Wipes, VWR Light-Duty Tissue Wipers, Technicloth Wipers, newspaper, any other paper that does not include binders, cloth, and porous polymer film. In general, any paper that is compatible with the selected patterning method may be used. In certain embodiments, porous, hydrophilic layers include Whatman chromatography paper No. 1.

In some embodiments, the electrode and the hydrophilic regions can be treated with chemicals to increase the hydrophilicity. Non-limiting examples of such chemical agents include 3-aminopropyldimethylethoxysilane (APDES).

Non-limiting examples of fluid-impermeable material comprise wax and polymerized photoresist. The photoresist used for patterning porous, hydrophilic material include SU-8 photoresist, SC photoresist (Fuji Film), poly(methylmethacrylate), nearly all acrylates, polystyrene, polyethylene, polyvinylchloride, and any photopolymerizable monomer that forms a hydrophobic polymer.

Figure 2:
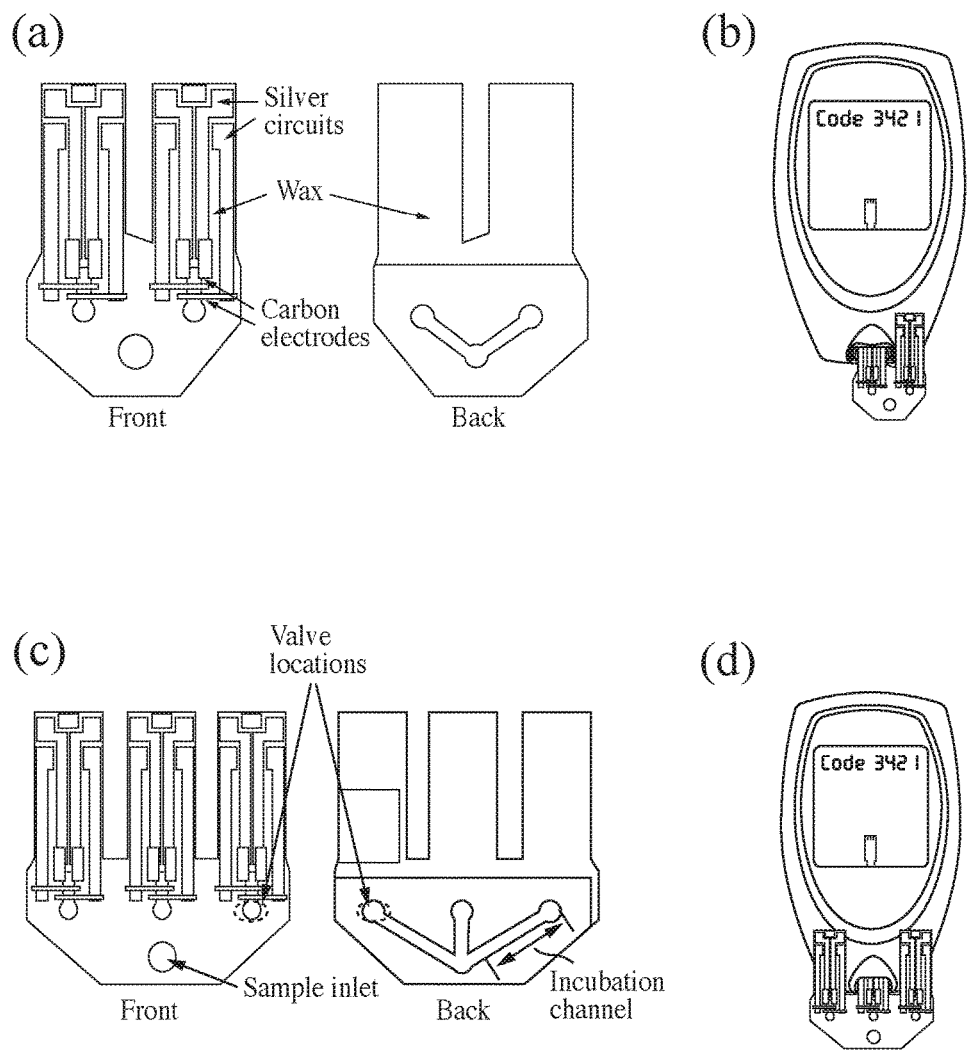
FIG. 2 illustrates paper-based microfluidic devices for multiplexed electrochemical assay using a commercial glucometer. (a) a paper-based microfluidic device with two testing strips each comprising an electrode assembly and a reaction channel; (b) the paper-based microfluidic device in (a) used in conjunction with a Glucometer; (c) a paper-based microfluidic device with three testing strips each comprising an electrode assembly and a reaction channel; (d) the paper-based microfluidic device used in (c) conjunction with a Glucometer.

In some embodiments, patterned paper-based microfluidic channels can be fabricated by wax-printing on chromatography paper. The fabrication process is simpler and less expensive, compared to the photolithography technique used in cleanroom. As shown in FIG. 2, devices with 2 testing strips (FIG. 2(a)-(b)) and 3 testing strips (FIG. 2(c)-(d)) are fabricated and used with a glucose meter. The paper layer can be patterned by wax and the electrode may contain carbon electrodes. Silver circuits may be deposited on the patterned paper layer. The testing strips are sized and shaped to be insertable into a commercial glucose meter designed and fabricated two-channeled and three-channeled paper-based electrochemical devices to demonstrate their applications in multiplexed electrochemical detection, as shown in FIG. 2. In some embodiments, multiple layers of paper and tape are used to form a 3D microfluidic device for fluid delivery.

In another aspect, a kit is described, comprising a microfluidic, electrochemical device as described herein. The microfluidic device in the kit may contain 1, 2, 3, 4, 5, 6, 7, 8, 9, 10, 11, 12, or more testing strips each designed to test a analyte of interest. The kit may include a set of instructions for obtaining a readout by a glucose meter for a characteristic of the analyte(s) of interest. The instruction may indicate a relation between a current readout by the glucose meter and a concentration of the analyte. In some embodiments, the instruction is a standard calibration plot.

Experimental Section

Chemical Reagents

Carbon ink (E3456) and silver ink (E1660) were purchased from Ercon Inc (Wareham, Mass.) and Conductive Compound (Hudson, N.H.), respectively. D-glucose, L-lactate, cholesterol, ethanol (≥99.5%), Triton X-100, β-Nicotinamide adenine dinucleotide hydrate, glucose oxidase (136,300 units/mg, *Aspergillus niger*), lactate oxidase (>20 units/mg, *Pediococcus species*), alcohol dehydrogenase (≥300 units/mg, *Saccharomyces cerevisiae*), cholesterol oxidase (≥50 units/mg, *Brevibacterium* sp.), and potassium ferricyanide were purchased from Sigma-Aldrich, and used as received. Organic silane 3-aminopropyldimethyl-ethoxysilane used for surface modification was purchased from Gelest. Inc. (http://www.gelest.com/), and used as received. Single-donor human plasma was purchased from Innovative Research, Inc. (http://www.innov-research.com/innov2010/), and used as received. Stock solutions of β-D-glucose were prepared in a PBS buffer (pH 7.0) and allowed to mutarotate overnight before use.

Fabrication and Design of the Device

The testing strip was designed to fit into the port of the glucometer.

Paper-based microfluidic channels were fabricated by patterning paper (Whatman 1 Chr) using wax printing. The paper was printed a piece of paper with printer (xerox phaser 8560), baked it at 120° C. for 2 min. The printed wax melted and diffused into paper to form the hydrophobic barriers for paper channels. The enzyme-containing solution was spotted on top of the paper microchannel. The solution was distributed evenly in the paper channel due to the effects of capillary wicking. After the solution dried, the enzyme was uniformly absorbed into the paper, and the device was ready for use. Conducting circuits were directly screen-printed on paper from Ag ink. After the drying of the Ag ink, carbon electrodes (a working electrode, a counter electrode, and two internal reference electrodes) were screen-printed on paper with a small portion of the electrodes overlapping with conducting circuits.

The circuits on paper were designed to fit into the port of the glucose meter by mimicking the commercial configuration. Electrodes and circuits were fabricated by screen-printing carbon ink (or Ag ink for circuits) on patterned paper. A stencil was generated for printing by designing patterns of electrodes using Adobe Freehand®, followed by cutting the pattern into stencil film using a laser-cutter (VersaLASER VLS3.50, Universal Laser Systems Inc.). The stencil was placed on top of a single piece of patterned paper, and filled the openings of the stencil with Ag ink for producing conducting circuits. The ink was baked on a hotplate at 100° C. for 30 minutes. After the Ag ink dried. Carbon electrode was screen-printed carbon electrodes from carbon ink following the same procedures.

All amperometric measurements were performed with a True Track blood glucose meters purchased from CVS, and calibrated following the instruction manual before use. According to the manufacturer, the test measures glucose concentrations over the range 20 to 600 mg/dL (~1.1-33.3 mmol/L). True Track blood glucose meters (glucometer is: i) low-cost (it is supplied free with the test strips), and simple, ii) ease of reverse engineering the test format used in that device into a format that fit our needs (the way differs with the test—so one that required concentration for water might be different from one that worked with blood).

In testing, the test strip portion of the device was inserted into the port of the glucose meter, and the tip of the microfluidic device was dipped in a solution of analytes. The solution of analytes wicked along the microfluidic channel, and distributed and mixed well with the pre-loaded reagents. After 10 seconds, the meter displayed reading. All measurements were conducted under ambient conditions.

Detection Method and Principle

The concentration of D-glucose (and L-Lactate) on was measured by the testing strip using the amperometric method with glucose meter as the electrochemical reader.

The enzymatic reaction happens spontaneously when the bodyfluid meet the pre-deposited reagents. The glucose meter measured the current generated by the oxidation of $Fe(CN)_6^{4-}$ in $Fe(CN)_6^{3-}$ at the anode, where a positive potential is applied by the glucometer. The reactions for the D-glucose and L-Lactate detection were:

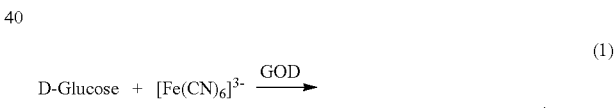

(1)

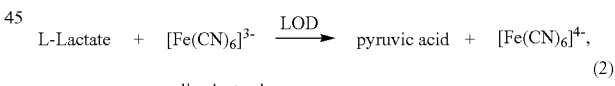

(2)

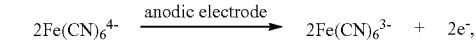

In the enzyme-catalyzed step, glucose (or other) oxidase (GOD) catalyzed the oxidation of glucose to gluconic acid (or lactate oxidase (LOD) catalyzed the oxidation of L-Lactate to pyruvicacid) with the concomitant reduction of Fe(III) to Fe(II) (eq 1); The $Fe(CN)_6^{4-}$ ions generated were detected chronoamperometrically (eq 2).

Figure 9:
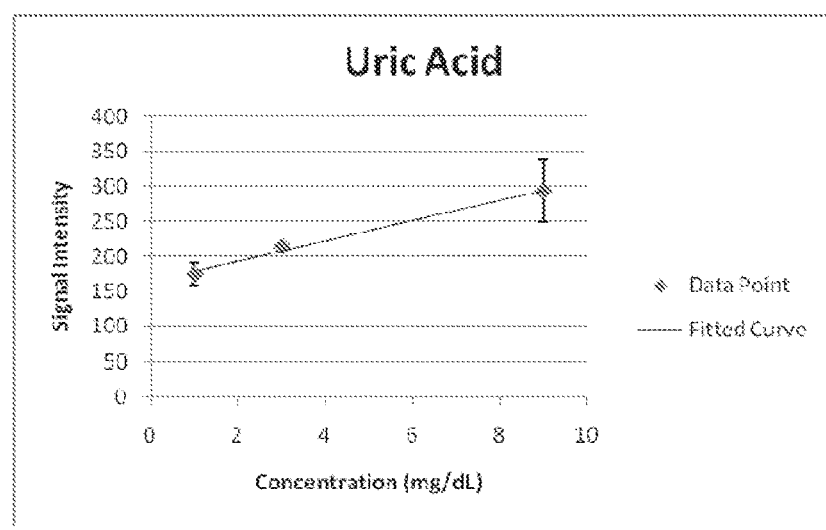
FIG. 9 illustrates a calibration plot for analyte uric acid.
Figure 10:
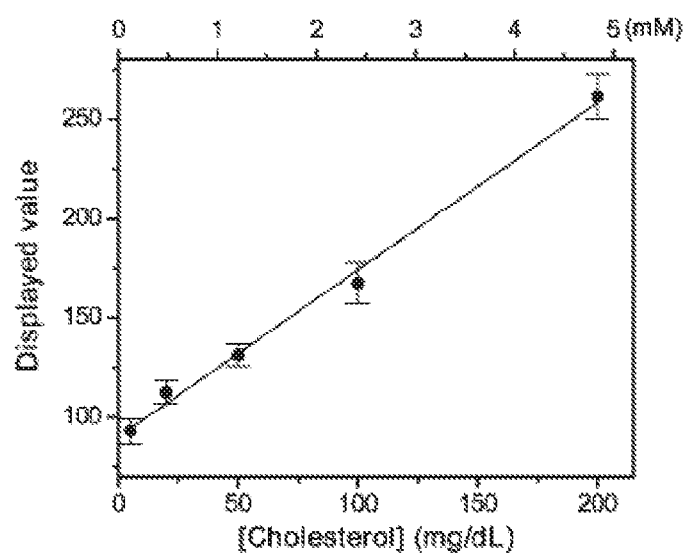
FIG. 10 illustrates a calibration plot for analyte cholesterol.

The device used herein can be used to test non-glucose analytes. The analyte can be selected so that its reaction with a reagent deposited in the reaction zone may generate an ion detectable by the glucometer, e.g., $Fe(CN)_6^{4-}$. For instance, a standard calibration curve for uric acid is shown in FIG. 9.

The concentration of cholesterol in human plasma is less than 5.2 mM (200 mg dL$^{-1}$). The analysis of cholesterol in human plasma using cholesterol oxidase yielded a linear calibration plot in the concentrations ranging from 20-200 mg dL$^{-1}$ (0.5-5.2 mM); 3 these values cover the clinically relevant range of cholesterol concentrations (FIG. 3). The limit of detection was 13 mg dL$^{-1}$ (0.34 mM) and the sensitivity was approximately 0.8 unit per mg dL$^{-1}$. The mean coefficient of variation of these analyses was about 6.2% (n=7).

Figure 11:
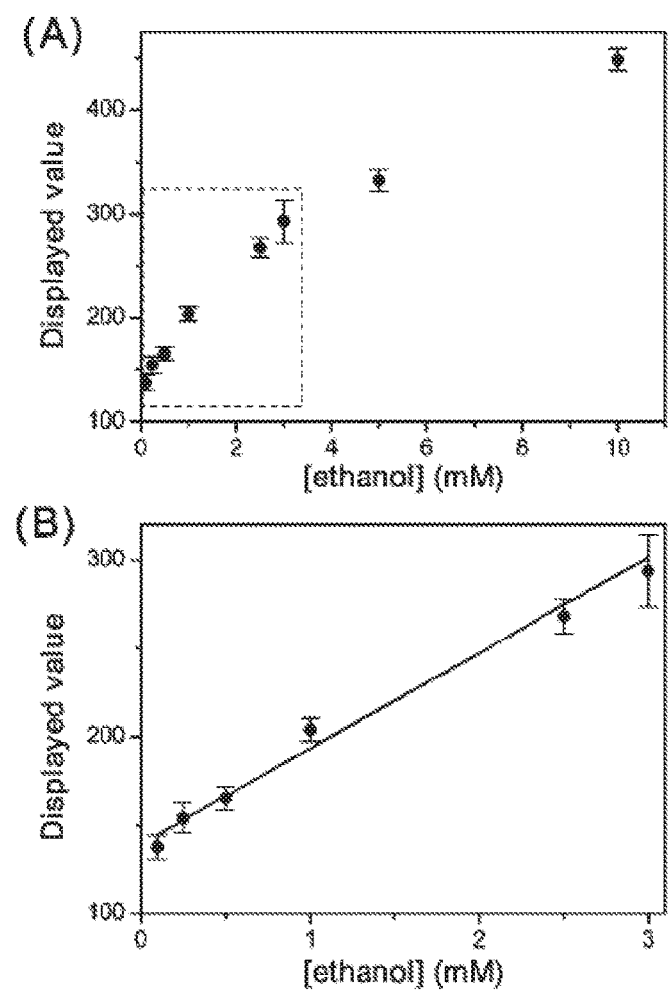
FIGS. 11A and 11B illustrates a calibration plots for analyte ethanol.

The electrochemical system has the potential to be useful in food quality control. A microfluidic device was used with glucometer to measure the concentration of ethanol. The calibration plot for the analysis of ethanol (FIGS. 11A and B) showed a linear range from 0.1 to 3 mM (R$^2$=0.970) with a sensitivity of 54 units per mM. The limit of detection was 0.1 mM, and the coefficient of variation ranged from 3.2% to 10.1%.

Equation (3) shows a generalized reaction for the measurement of glucose, lactate, and cholesterol.

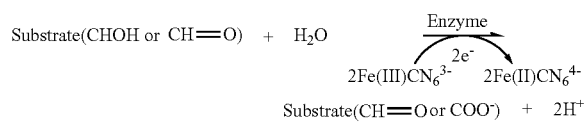

(3)

Equation (4) shows a reaction for the measurement of ethanol.

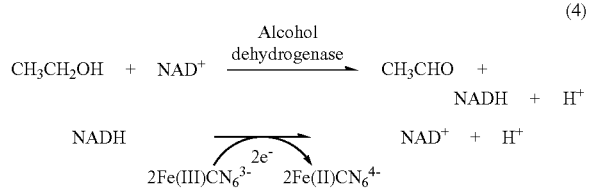

(4)

Fluid Control Using Paper-Based Cavity Valves

Equation (5) shows a reaction for the measurement of uric acid.

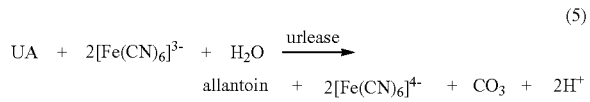

(5)

As the glucometer can only allow one readout at a time, cavity valves were designed on paper to control fluids for multiplexed assays. When layers of paper and tape were stacked to assemble the 3-D paper-based device, there is a small gap (i.e. the cavity, ~170 μm in height) perforated by laser-cutting in the middle layer of paper, as shown in FIG. 3a. Fluid will not flow across the cavity between top test zones and bottom incubation channels, which set the cavity valves to sit in the 'off' status. This will allow enzymatic reactions that need longer reaction time than 10 second to complete on chip before reaching test zones. When pressing a valve using a modest mechanical force, the gap is closed because of the deformation of the top layer of paper (see FIG. 3a). The test zone on the top layer of paper gets in contact with the incubation channel on the bottom layer of paper, and thus the valve is actuated to be on. The sample in the incubation channel can be delivered by wicking effect to the test zone for the amperometric detection (FIG. 3b).

Figure 4:
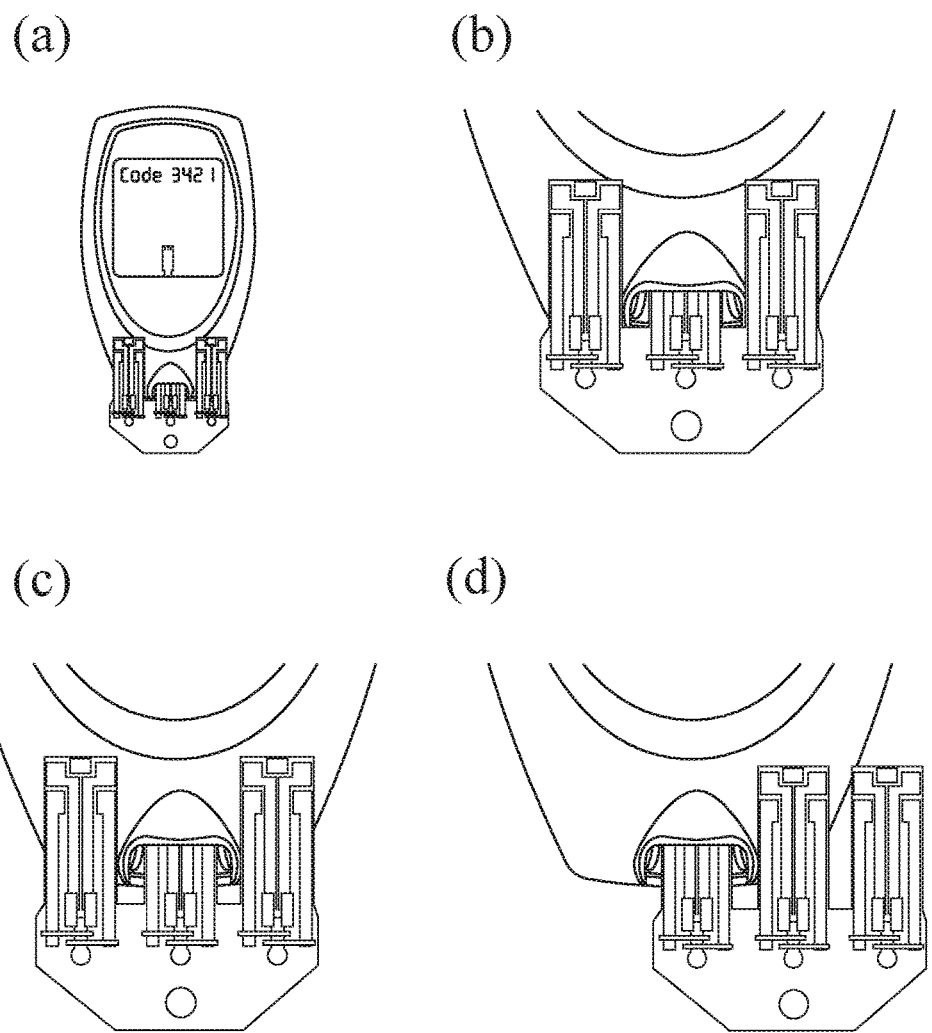

FIG. 4 shows how the fluids on a 3D microfluidic paper-based device were controlled to deliver a sample to different detection zones sequentially. A solution of red food dye was used to mimic a blood sample for this demonstration. When the sample was just loaded, the test zones on the top layer of paper were not connected with the incubation channels on the bottom layer, because of the gap in the middle layer of paper (FIG. 3a). So the fluid stayed only on the bottom layer of paper, but not on the top layer of paper (FIG. 4b). When the central 'button' was pushed, the central cavity valve was turned on, so the sample was delivered to the central detection zone, as shown by the color change from white to red in the central test zone in FIG. 4c and FIG. 3b. Because the other two valves were still off, those two test zones stayed white.

Likewise, the sample was delivered to the left test zone via turning on the left valve (FIG. 4d). The commercial glucometer has certain requirement on the flow rate. If the flow is too slow in the test zone, the glucometer will pop up error information. In order to improve the flow rate, the platform was optimized by (i) minimizing the channel length, (ii) treating both test zones and incubation channels with APDES, (iii) minimizing the number of cavity valves for each test unit, and (iv) sealing the front test zones with tape to enhance the capillary effect.

The assays are programmable by choosing different enzymes to prestore in different incubation channels. For example, in the 2-plexed assay, the combination of glucose and cholesterol, glucose and lactate, or cholesterol and lactate can be chosen.

The paper-based devices are compliant. It can be bended so that one branch is inserted to the port of a glucometer, without damaging electrodes and circuits on other branches (See FIGS. 4b and 4d). This property is suitable to multiplexed assays in a compact format, which is advantageous to commercial plastic strips because those plastic strips are relatively hard to bend. The multiple testing strips in a device are attached to each to each other and can support each other.

Figure 5:
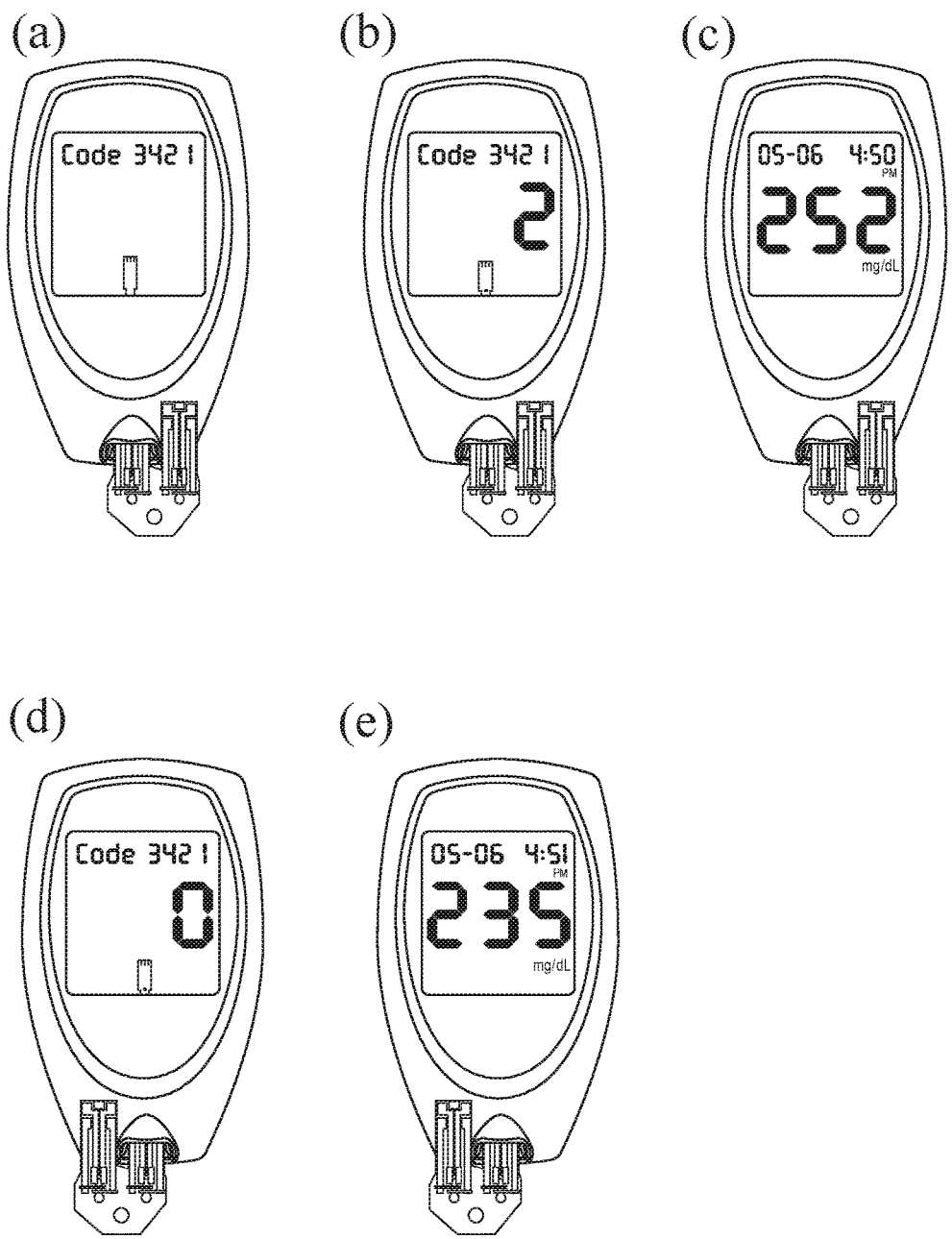
FIG. 5 shows a glucose testing of glucose (250 mg/dL) in artificial plasma using Glucometer and a microfluidic device with two testing strips. (a) before testing; (b) the glucometer started to a 2-second countdown before the assay; (c) the analysis result for the left testing strip; (d) the glucometer started to count down for the right test unit, "0" refers to 0 second; (e) The analysis result for the right testing strip.

The device was tested by measuring glucose using a 2-plexed testing strip and a glucometer. A series of photographs in FIG. 5 shows the 2-plexed analysis process and results. The left test unit gave a similar result to the right one. Four-time 2-plexed assays gave eight data points and an average of 246±15 mg/dL (n=8), indicating consistent results among different assays. After assay, the data including the date were stored in the glucometer for future tracking.

FIG. 5 illustrates a device validation by measuring glucose (250 mg/dL) in artificial plasma. (a) Before test. (b) The glucometer started to count down. "2" refers to 2-second countdown before the assay. The glucometer has a 10-second countdown step before assays, once a sample is sensed by the glucometer. (c) The analysis result for the left channel. (d) The glucometer started to count down for the right test unit. "0" refers to 0 second. (e) The analysis result for the right channel.

Surface Treatment of Electrodes by APDES

A 1.0 μL solution of 2 wt % APDES (3-aminopropyldimethylethoxysilane) in water was added to each test zone. The solution was allowed to dry for 10 min at room temperature. Another 1.0 μL solution of APDES was used to treat the device for a second time following the same procedure. Meanwhile, each incubation channel on the bottom layer was treated with 1.2 μL APDES once.

Procedures of Multiplexed Assay of Glucose, Cholesterol, and Lactate

Different enzymes were first prestored on different incubation channels on the bottom layer of paper, and let them dry under ambient conditions. Before assays, equal volume of 160 mM $K_3Fe(CN)_6$ in water and a mixture sample containing glucose, cholesterol, and lactate were mixed. Once the sample was spot on the sample inlet, the central 'button' was pushed to start the glucose assay first. As to the assays for cholesterol and lactate, 1 min was allowed to complete enzymatic reactions for cholesterol and lactate on chip before their assays were started. The reaction can be completed in less time, the system was designed to be one minute to ensure excess time for the metabolites (lactate or cholesterol) to be transformed by the enzyme in totality.

In order to fit the capability of the glucometer to our electrode geometry, the dimensions of the testing strips was adjusted to make the measured currents fit the desired range of concentrations. In principle, the same objective might be achieved by reprogramming the software of the chip.

The feasibility of using a self-monitoring glucometer was evaluated for measuring the concentration of a wide range of analytes including glucose and lactate in the testing strip.

The application of the electrochemical analytical system in measuring various other analytes such as cholesterol, phenolic compounds, ethanol, and uric acid was explored.

The electrical current was tuned by varying the surface area of the working electrode to match the readout of electrochemical detection in the testing strip without the adjustment of the internal settings of glucose meters. Based on the Cottrell equation, the electrical current, i, of electrochemical detection is linearly proportional to the surface area, A, of electrode as $i \infty A$.

Figure 7A:
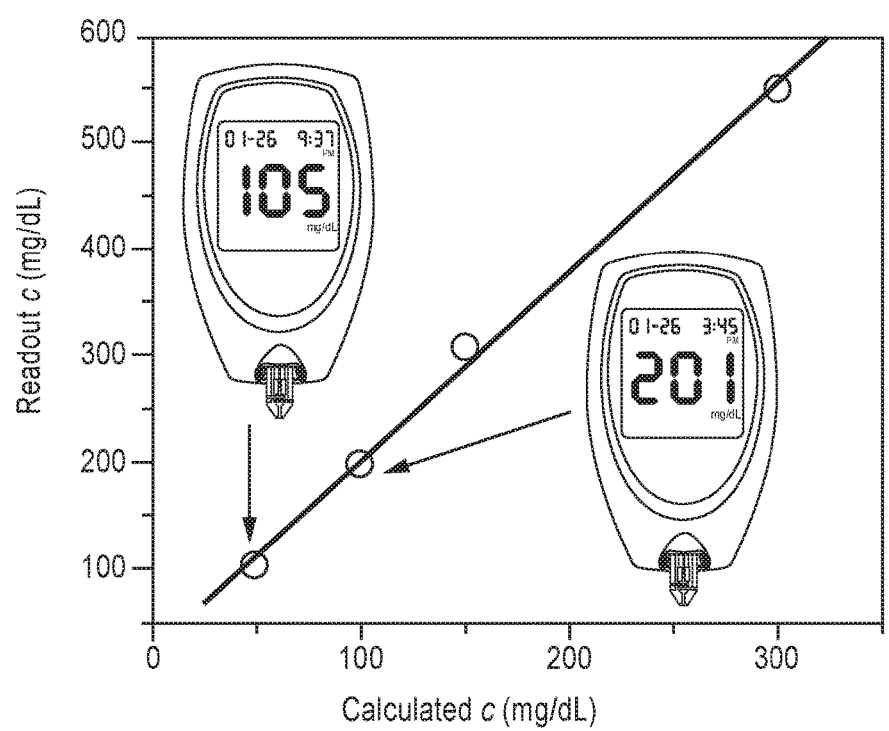
FIG. 7(A) is a calibration plot for the analysis of glucose in a microfluidic device using commercial Glucometer.
Figure 7B:
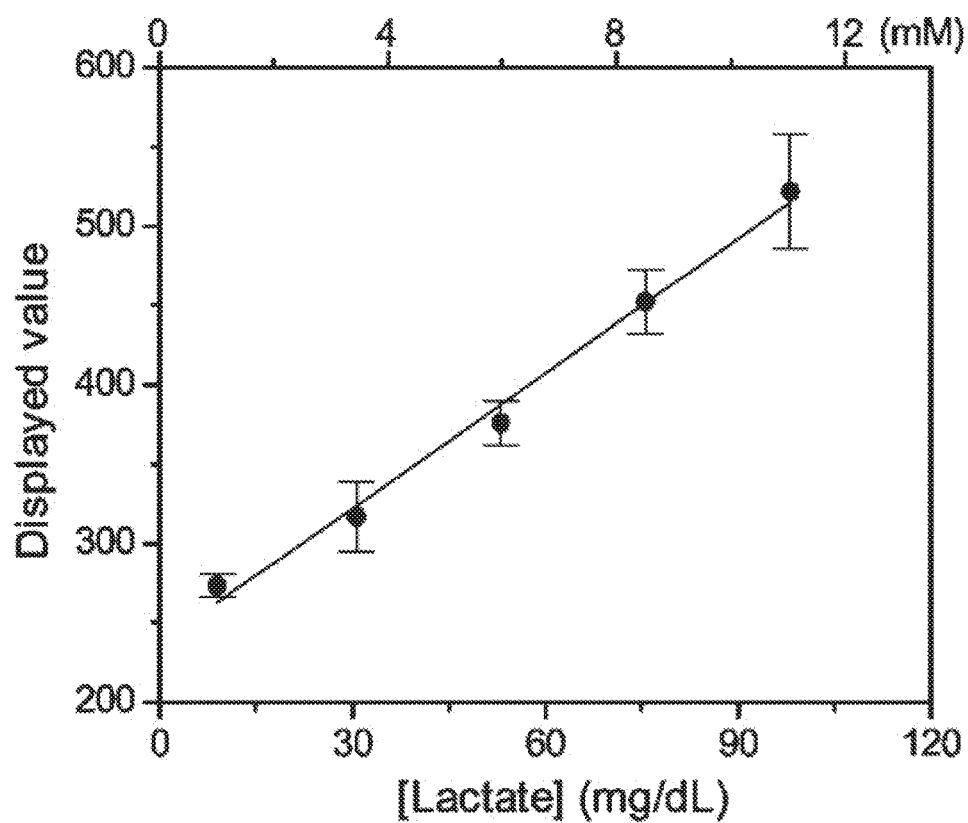
FIG. 7(B) is a calibration plot for the analysis of lactate in a microfluidic device using commercial Glucometer.

Calibration curves were generated for the measurement of glucose (FIG. 7A) and lactate (FIG. 7B) in aqueous solutions in the testing strips using glucometer. The readout of glucose concentration, $c_{read}$ from glucometer increases proportionally with the concentration of glucose, $c_{real}$, which yields a linear calibration plot with a slope of 1.78 (correlation coefficient, 0.996). So that the concentration of glucose, $c_{real}$ can be obtained from $c_{real}=c_{read}/1.78$.

Optimization of the Design of Microfluidic Paper-Based Electrochemical Device

Figure 8:
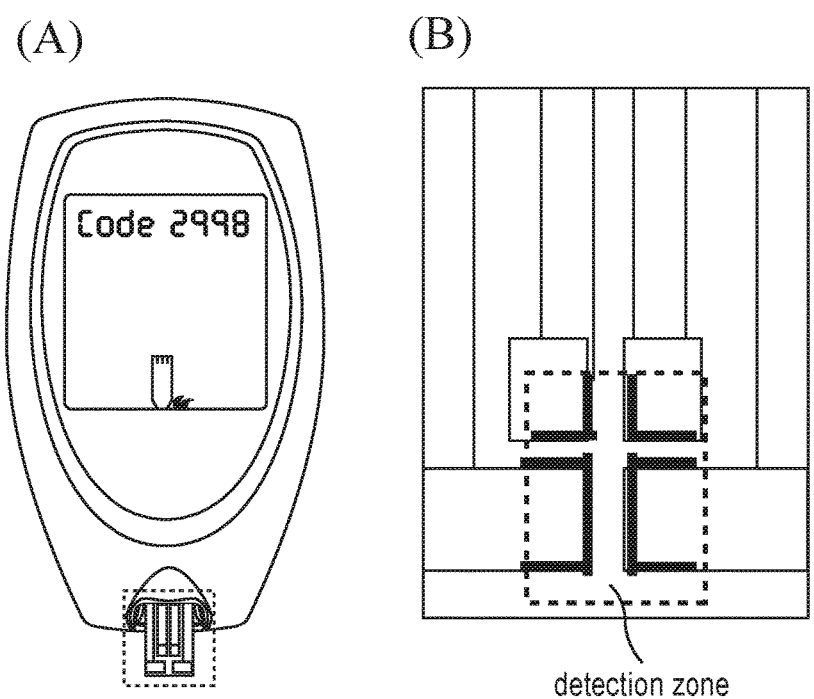
FIG. 8 (A) shows a microfluidic device made from a single layer of paper channel inserted into the test port of a Glucometer; (B) shows a photography of a detection zone of the microfluidic device (area in the square in A).

Single layer microfluidic device made from a single layer of paper channels was studied for the electrochemical measurement of analytes (FIG. 8A, B), since the single layer platform is relatively easy to fabricate and uses less solution of analytes. However, when a solution of analytes wicked in the paper channels, the solution only wet the edge portion of the electrodes (as indicated by the blue lines in FIG. 8B), which substantially decreased the effective working area of the electrodes. This issue maybe sovled by using a chemical such as APDES to treat the electrode to increase its hydrophilicity.

Figure 6:
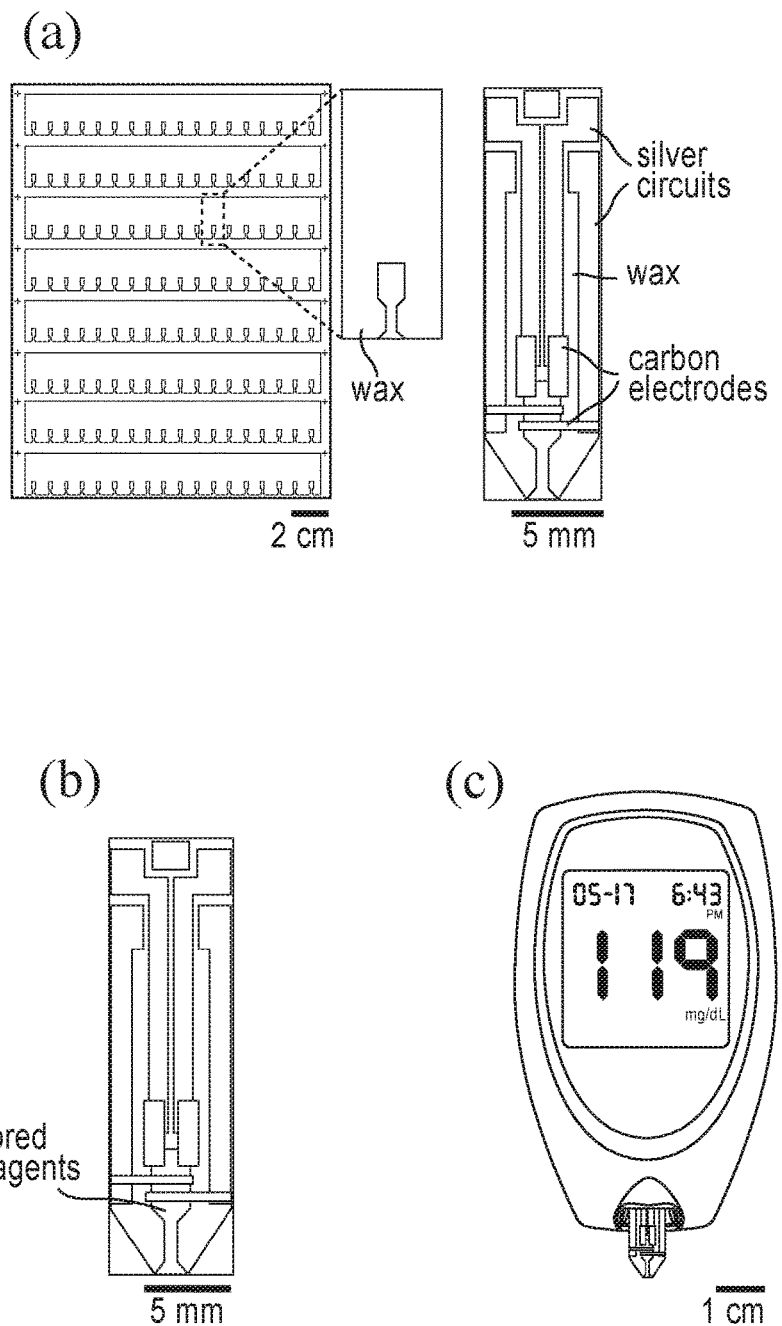
FIG. 6 shows a microfluidic device using a glucometer as electrochemical reader. (A) The fabrication of the microfluidic device. (B) the microfluidic device has reagents stored in one of its hydrophilic regions; (C) the microfluidic device is inserted into the test port of the device and the glucose meter displays the result of measurement in mg/dL.

A microfluidic device as described herein is shown in FIG. 6. The device includes microfluidic channels, electrodes, and electrical interconnects fabricated in chromatography paper using wax printing and screen printing (FIGS. 6A and B). The wires were printed using silver ink, and four electrodes (a working electrode, a counter electrode, and two auxiliary electrodes) were printed using graphite ink. The chemical reagents needed for the assays of glucose or other analytes of interest and alcohol were stored in the detection zone of the device. To use this system, the dry device was usually inserted into the port of the glucose meter. After a drop of fluid to the exposed end of the device was applied and the liquid containing the analytes was allowed to wick to its sensing region, the glucose meter initiated amperometric measurement, and displayed the electrochemical readout on its LCDscreen (FIG. 6C). In some reactions (e.g., those for lactate and cholesterol), when the time interval required to complete the enzymatic reactions was greater than the 10 second waiting-time set in the glucometer, the solution of analytes can be mixed with the chemical reagents needed for the assays in a small centrifuge tube (the mixing can also be conducted on any clean substrate such as a plastic thin film or the surface of a table), and the reaction was allowed to proceed to completion. A dry device was inserted into the port of the glucometer, and the depositon zone was dipped the exposed into this reacted solution to perform the analysis.

Different formulations of conductive ink can be used as electrodes or electrical contact. It allows an adaptation of the design of the microfluidic devices to obtain a suitable current range for the glucometer depending of the relevant concentrations range of the detected analytes.

Upon review of the description and embodiments of the present invention, those skilled in the art will understand that modifications and equivalent substitutions may be performed in carrying out the invention without departing from the essence of the invention. Thus, the invention is not meant to be limiting by the embodiments described explicitly above, and is limited only by the claims which follow.

What is claimed is:

1. A microfluidic, electrochemical device comprising
   two or more porous, hydrophilic layers comprising at least a first and a second porous, hydrophilic layers and comprising a fluid-impermeable material that defines a plurality of test channels comprising at least a first test channel and a deposition zone within the porous, hydrophilic layer;
   a plurality of reaction zones comprising at least a first reaction zone for detecting a first analyte and defined by a fluid impermeable material in a porous hydrophobic layer, the first reaction zone in fluid communication with the deposition zone through the first test channel; and
   a plurality of electrode assemblies comprising a first electrode assembly comprising one or more electrode(s) in fluidic communication with the first reaction zone, said electrodes sized to provide current signals readable by an electrochemical reader;
   wherein the deposition zone, the first reaction zone and the first electrode assembly are on the same or different hydrophilic layers, and
   wherein at least a portion of the device is sized and arranged to be insertable into an electrochemical reader;
   wherein the deposition zone and each of the reaction zone(s) are in fluid contact through a valve capable moving from a first non-fluid-communicating position to a second fluid-communicating position; and
   wherein the valve comprises a spacer layer disposed between the first and second porous, hydrophilic layers, said spacer layer comprising an opening in alignment with at least a portion of the respective reaction zone and testing channel.

2. The microfluidic, electrochemical device of claim 1, wherein the first reaction zone includes one or more reagents for detecting the first analyte.

3. The microfluidic, electrochemical device of claim 1, wherein the first analyte is selected from the group consisting of lactate, ethanol, uric acid, urea, creatinine, creatine, glucose, cholesterol, pyruvate, creatinine, β-hydroxybutyrate, alanine aminotrasferase, aspartate aminotransferase, alkaline phosphatase, and acetylcholinesterase, and their inhibitors.

4. The microfluidic, electrochemical device of claim 1, further comprises
- a second test channel defined by the fluid impermeable material; and
- a second reaction zone for detecting a second analyte and defined by a fluid impermeable material in a porous hydrophobic layer, the second reaction zone in fluid communication with the deposition zone through the second test channel; and
- a second electrode assembly comprising one or more electrode(s) in fluidic communication with the second reaction zone, said electrodes sized to provide current signals readable by an electrochemical reader.

5. The microfluidic, electrochemical device of claim 4, wherein the second reaction zone includes one or more reagents for detecting the second analyte.

6. The microfluidic, electrochemical device of claim 4, wherein the first and the second analytes are the same or different.

7. The microfluidic, electrochemical device of claim 4, wherein the second analyte is not glucose.

8. The microfluidic, electrochemical device of claim 4, wherein the second analyte is selected from the group consisting of lactate, ethanol, uric acid, urea, creatinine, creatine, glucose, cholesterol, pyruvate, creatinine, β-hydroxybutyrate, alanine aminotrasferase, aspartate aminotransferase, alkaline phosphatase, and acetylcholinesterase, and their inhibitors.

9. A method of detecting a first and a second analytes, comprising:
- providing the device of claim 4 capable of detecting first and second analytes;
- depositing a fluidic sample in the depositing zone;
- contacting the device with an electrochemical reader;
- obtaining a readout by the electrochemical reader indicative of the concentration of the first analyte based on a first set of instructions; and
- obtaining a readout by the electrochemical reader indicative of the concentration of the second analyte based on a second set of instructions.

10. The microfluidic, electrochemical device of claim 4, further comprises
- a third test channel defined by the fluid impermeable material; and
- a third reaction zone for detecting a third analyte and defined by a fluid impermeable material in a porous hydrophobic layer, the third reaction zone in fluid communication with the deposition zone through the third test channel; and
- a third electrode assembly comprising one or more electrode(s) in fluidic communication with the third reaction zone, said electrodes sized to provide current signals readable by an electrochemical reader.

11. The microfluidic, electrochemical device of claim 10, wherein the third reaction zone includes one or more reagents for detecting the third analyte.

12. The microfluidic, electrochemical device of claim 10, wherein the first, second, and third analytes are the same or different.

13. The microfluidic, electrochemical device of claim 10, wherein the third analyte is not glucose.

14. The microfluidic, electrochemical device of claim 10, wherein the third analyte is selected from the group consisting of lactate, ethanol, uric acid, urea, creatinine, creatine, glucose, cholesterol, pyruvate, creatinine, β-hydroxybutyrate, alanine aminotrasferase, aspartate aminotransferase, alkaline phosphatase, and acetylcholinesterase, and their inhibitors.

15. A method of detecting a first, second, and additional analyte(s), comprising:
- providing the device of claim 10 capable of detecting first, second and third analytes;
- depositing a fluidic sample in the depositing zone;
- contacting the device with an electrochemical reader;
- obtaining a readout by the electrochemical reader indicative of the concentration of the first analyte based on a first set of instructions;
- obtaining a readout by the electrochemical reader indicative of the concentration of the second analyte based on a second set of instructions; and
- obtaining readout(s) by the electrochemical reader indicative of the concentration of the third analyte based on an additional set(s) of instructions.

16. The microfluidic, electrochemical device of claim 10, further comprises
- additional test channel(s) defined by the fluid impermeable material; and
- additional reaction zone(s) for detecting additional analyte(s) and defined by a fluid impermeable material in a porous hydrophobic layer, the reaction zone in fluid communication with the deposition zone through the test channel; and
- additional electrode assemblies each comprising one or more electrode(s) in fluidic communication with the respective reaction zone, said electrodes sized to provide current signals readable by an electrochemical reader.

17. The microfluidic, electrochemical device of claim 16, wherein the additional reaction zone includes one or more reagents for detecting the additional analytes.

18. The microfluidic, electrochemical device of claim 16, wherein, wherein the first second, third, and additional analytes are the same or different.

19. The microfluidic, electrochemical device of claim 16, wherein the additional analyte(s) are not glucose.

20. The microfluidic, electrochemical device of claim 16, where additional analyte is selected from the group consisting of lactate, ethanol, uric acid, urea, creatinine, creatine, glucose, cholesterol, pyruvate, creatinine, β-hydroxybutyrate, alanine aminotrasferase, aspartate aminotransferase, alkaline phosphatase, and acetylcholinesterase, and their inhibitors.

21. The microfluidic, electrochemical device of claim 16, comprises
- at least 12 test channels; and
- at least 12 reaction zones for detecting 12 analyte(s), respectively, and each of the reaction zone is in fluid communication with the deposition zone through the respective test channels; and
- at least 12 electrode assemblies each comprising one or more electrode(s) in fluidic communication with the respective reaction zone, said electrodes sized to provide current signals readable by an electrochemical reader.

22. The microfluidic, electrochemical device of claim 1, wherein the deposition zone and any of the reaction zones are not in fluid communication when the valve connecting the deposition zone and the reaction zone is at the first non-fluid-communicating position.

23. The microfluidic, electrochemical device of claim 1, wherein the reagent is selected to react with the analyte to generate an intermediate reducible or oxidizable by the electrode.

24. The microfluidic, electrochemical device of claim 1, wherein the analyte is reduced or oxidized.

25. The microfluidic, electrochemical device of claim 1, wherein the hydrophilic layer comprises paper.

26. The microfluidic, electrochemical device of claim 1, wherein the fluid-impermeable material comprises polymerized photoresist.

27. The microfluidic, electrochemical device of claim 1, wherein electrochemical reader is a glucose meter.

28. A method of detecting a first analyte, comprising:
providing the device of claim 1 capable of detecting a first analyte;
depositing a fluidic sample in the depositing zone;
contacting the device with an electrochemical reader; and
obtaining a readout by the electrochemical reader indicative of the concentration of the first analyte based on a first set of instructions.

29. The method of claim 28, further comprising:
actuating a valve from a first non-fluid communicating position to a second fluid-communicating position to enable fluid contact between the deposition zone and the reaction zone(s).

30. The method of claim 28, wherein electrochemical reader is a glucose meter.

31. A kit comprising:
a microfluidic, electrochemical device comprising
a first porous, hydrophilic layer comprising a fluid-impermeable material that defines a plurality of test channels comprising at least a first test channel and a deposition zone within the first porous, hydrophilic layer;
a second porous, hydrophilic layer disposed over the first layer comprising:
a fluid-impermeable material that defines a plurality of reaction zones comprising at least a first reaction zone including one or more reagents for detecting a first analyte, the deposition zone in fluid communication with the first reaction zone through the first test channel; and
a plurality of electrode assemblies comprising a first electrode assembly comprising one or more electrode(s) in fluidic communication with the first reaction zone, said electrodes sized to provide current signals readable by an electrochemical reader; and
a first set of instructions for obtaining a readout by the electrochemical reader for a characteristic of the first analyte; wherein
the first porous, hydrophilic layer further comprises a second test channel; and
the second porous, hydrophilic layer further comprises
a second reaction zone including one or more reagents for detecting a second analyte, the deposition zone in fluid communication with the second reaction zone through the second test channel; and
a second electrode assembly comprising one or more electrode(s) in fluidic communication with the second reaction zone, said electrodes sized to provide current signals readable by an electrochemical reader; and
the kit further comprises a second set of instructions for obtaining a readout by the electrochemical reader for a characteristic of the second analyte.

32. The kit of claim 31, wherein the first set of instructions indicates a relation between a current readout by the electrochemical reader and a concentration of the first analyte.

33. The kit of claim 31, wherein the first analyte is selected from the group consisting of lactate, ethanol, uric acid, urea, creatinine, creatine, glucose, cholesterol, pyruvate, creatinine, β-hydroxybutyrate, alanine aminotrasferase, aspartate aminotransferase, alkaline phosphatase, and acetylcholinesterase, and their inhibitors.

34. The kit of claim 31, wherein the second set of instructions indicates a relation between a current readout by the electrochemical reader and a concentration of the second analyte.

35. The kit of claim 31, wherein the first and the second analytes are the same or different.

36. The kit of claim 31, wherein the second analyte is not glucose.

37. The kit of claim 31, wherein the first or second analyte is selected from the group consisting of lactate, ethanol, uric acid, urea, creatinine, creatine, glucose, cholesterol, pyruvate, creatinine, β-hydroxybutyrate, alanine aminotrasferase, aspartate aminotransferase, alkaline phosphatase, and acetylcholinesterase, and their inhibitors.

38. The kit of claim 31, wherein
the first porous, hydrophilic layer further comprises a third test channel; and
the second porous, hydrophilic layer further comprises:
a third reaction zone each including one or more reagents for detecting a third analyte, the deposition zone in fluid communication with the third reaction zone through the third test channel; and
a third electrode assembly comprising one or more electrode(s) in fluidic communication with the third reaction zone, said electrodes sized to provide current signals readable by an electrochemical reader; and
the kit further comprises a third set of instructions for obtaining readouts by the electrochemical reader for a characteristic of the third analyte.

39. The kit of claim 38, wherein the third set of instructions indicates a relation between a current readout by the electrochemical reader and a concentration of each additional analyte.

40. The kit of claim 38, wherein the first, second, and third analytes are the same or different.

41. The kit of claim 38, wherein the third analyte is not glucose.

42. The kit of claim 38, wherein the first, second, or third analyte is selected from the group consisting of lactate, ethanol, uric acid, urea, creatinine, creatine, glucose, cholesterol, pyruvate, creatinine, β-hydroxybutyrate, alanine aminotrasferase, aspartate aminotransferase, alkaline phosphatase, and acetylcholinesterase, and their inhibitors.

43. The kit of claim 38, wherein
the first porous, hydrophilic layer further comprises additional test channel(s); and
the second porous, hydrophilic layer further comprises:
additional reaction zone(s) each including one or more reagents for detecting additional analyte(s), the deposition zone in fluid communication with the additional reaction zone(s) through the respective additional test channel(s); and
additional electrode assemblies each comprising one or more electrode(s) in fluidic communication with the respective additional reaction zone, said electrodes sized to provide current signals readable by an electrochemical reader; and the kit further comprises additional set(s) of instructions for obtaining readout(s) by the electrochemical reader for a characteristic of the additional analyte(s).

44. The kit of claim 43, wherein the additional set(s) of instructions indicate a relation between a current readout by the electrochemical reader and a concentration of each additional analyte.

45. The kit of claim 43, wherein the first, second, third, and additional analytes are the same or different.

46. The kit of claim 43, wherein the additional analyte(s) are not glucose.

47. The kit of claim 43, wherein the first, second, third, or additional analyte is selected from the group consisting of lactate, ethanol, urea, creatinine, creatine, glucose, cholesterol, pyruvate, creatinine, β-hydroxybutyrate, alanine aminotrasferase, aspartate aminotransferase, alkaline phosphatase, and acetylcholinesterase, and their inhibitors.

48. The kit of claim 43, wherein
the first porous, hydrophilic layer comprises at least 12 test channels;
the second porous, hydrophilic layer comprises
at least 12 reaction zone(s) each including one or more reagents for detecting 12 analytes, the deposition zone in fluid communication with the reaction zones through the respective test channels; and
at least 12 electrode assemblies each comprising one or more electrode(s) in fluidic communication with the respective reaction zone, said electrodes sized to provide current signals readable by an electrochemical reader; and
the kit further comprises at least 12 set(s) of instructions for obtaining readout(s) by the electrochemical reader for a characteristic of the 12 analyte(s), respectively.

49. The kit of claim 31, wherein the reagent is selected to react with the analyte to generate an intermediate reducible or oxidizable by the electrode.

50. The kit of claim 31, wherein the hydrophilic layer comprises paper.

51. The kit of claim 31, wherein the fluid-impermeable material comprises polymerized photoresist.

52. The kit of claim 31, wherein electrochemical reader is a glucose meter.

53. A kit comprising:
a microfluidic, electrochemical device comprising
a first porous, hydrophilic layer comprising a fluid-impermeable material that defines a plurality of test channels comprising at least a first test channel and a deposition zone within the first porous, hydrophilic layer;
a second porous, hydrophilic layer disposed over the first layer comprising:
a fluid-impermeable material that defines a plurality of reaction zones comprising at least a first reaction zone including one or more reagents for detecting a first analyte, the deposition zone in fluid communication with the first reaction zone through the first test channel; and
a plurality of electrode assemblies comprising a first electrode assembly comprising one or more electrode(s) in fluidic communication with the first reaction zone, said electrodes sized to provide current signals readable by an electrochemical reader; and
a first set of instructions for obtaining a readout by the electrochemical reader for a characteristic of the first analyte; wherein the deposition zone and each of the reaction zone(s) are in fluid contact through a valve capable moving from a first non-fluid-communicating position to a second fluid-communicating position.

54. The kit of claim 53, wherein the deposition zone and any of the reaction zones are not in fluid communication when the valve connecting the deposition zone and the reaction zone is at the first non-fluid-communicating position.

55. The kit of claim 54, wherein the valve comprises a spacer layer disposed between the first and second porous, hydrophilic layers, said spacer layer comprising an opening in alignment with at least a portion of the respective reaction zone and testing channel.

* * * * *